(12) United States Patent
Harada et al.

(10) Patent No.: US 6,169,209 B1
(45) Date of Patent: Jan. 2, 2001

(54) PREPARATION OF ORGANIC PHOSPHONIUM CHLORIDE

(75) Inventors: Katsumasa Harada; Ryoji Sugise; Koichi Kashiwagi; Sadao Niida, all of Yamaguchi (JP)

(73) Assignee: Ube Industries, Ltd., Yamaguchi (JP)

( * ) Notice: Under 35 U.S.C. 154(b), the term of this patent shall be extended for 0 days.

(21) Appl. No.: 09/200,370

(22) Filed: Nov. 23, 1998

(30) Foreign Application Priority Data

Nov. 21, 1997 (JP) .................................................. 9-321004

(51) Int. Cl.$^7$ ........................................................ C07F 9/54
(52) U.S. Cl. .................................................................. 568/9
(58) Field of Search ............................................. 568/8, 9

(56) References Cited

U.S. PATENT DOCUMENTS

| | | | |
|---|---|---|---|
| 3,755,459 | * 8/1973 | Diamond | ................... 568/9 |
| 4,520,204 | * 5/1985 | Evans | ................... 548/476 |
| 5,705,696 | * 1/1998 | King, Jr. | ................... 564/296 |
| 5,741,931 | * 4/1998 | Naumann | ................... 568/9 |

OTHER PUBLICATIONS

Journal of American Chem Soc by Willard vol. 70, pp 737–738, 1948.*

* cited by examiner

*Primary Examiner*—Jean F Vollano
(74) *Attorney, Agent, or Firm*—McAulay Nissen Goldberg & Kiel, LLP

(57) ABSTRACT

An improved process for preparing an organic phosphonium chloride is performed by bringing an organic phosphonium bromide into contact with a chloride ion in a heterogeneous mixture solution of water and an organic solvent.

9 Claims, No Drawings

PREPARATION OF ORGANIC PHOSPHONIUM CHLORIDE

FIELD OF THE INVENTION

The present invention relates to a process for preparing an organic phosphonium chloride. In particular, the invention relates to a process for preparing an organic phosphonium chloride from its corresponding organic phosphonium bromide.

BACKGROUND OF THE INVENTION

The organic phosphonium chloride is of value as a catalyst for various reactions, for instance, an interphasic transfer catalyst, a polymerization catalyst, and a transhalogenation catalyst.

It is known that the organic phosphonium chloride can be prepared starting from a corresponding organic phosphonium bromide.

J. Am. Chem. Soc., 70, pp. 737 (1948) describes a process for preparing an organic phosphonium chloride by treating an organic phosphonium bromide with an ion exchange resin. This process, however, has some drawbacks in that a great amount of ion exchange resin is required, the ion exchange resin has to be regenerated every cycle, and a great amount of aqueous waste such as an aqueous solution containing a chloride ion and a bromide ion is produced. Moreover, the obtained organic phosphonium chloride has to be recrystallized from an appropriate organic solvent for purification, and the yield is up to 79%.

Nippon Kagaku Zasshi (Chemistry Magazine of Japan, in Japanese), 86, pp. 112 (1965) describes a process for preparing an organic phosphonium chloride by the steps of converting an organic phosphonium bromide to its corresponding organic phosphonium fluoroborate and treating the fluoroborate with potassium chloride to give the desired phosphonium chloride. This process, however, has drawbacks in that an expensive silver borofluoride is required in a stoichiometric amount for the desired conversion, and that the produced phosphonium chloride has to be repeatedly recrystallized from an appropriate organic solvent.

SUMMARY OF THE INVENTION

It is an object of the present invention to provide an improved process for preparing an organic phosphonium chloride from an organic phosphonium bromide.

Specifically, it is an object of the invention to provide a process for the preparation of an organic phosphonium chloride in a high yield, using no expensive chemical compound and no complicated procedures.

The present invention resides in a process for preparing an organic phosphonium chloride which comprises bringing an organic phosphonium bromide into contact with a chloride ion in a heterogeneous mixture solution comprising water and an organic solvent.

DETAILED DESCRIPTION OF THE INVENTION

The organic phosphonium bromide employed in the process of the invention is represented by the following formula (I):

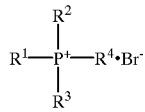

In the formula (I), $R^1$, $R^2$, $R^3$ and $R^4$ independently represents an aryl group, an aralkyl group, an alkyl group, or a heterocyclic group.

The organic phosphonium bromide can be prepared by the known reaction between a tertiary phosphine and a bromine-containing compound. See Chem. Ber. 99, pp. 2782 (1966).

Details of the organic phosphonium bromide having the formula (I) are given below.

The aryl group can have 6 to 14 carbon atoms. Examples of the aryl groups include phenyl, biphenyl, and naphthyl.

The aralkyl group can have 7 to 15 carbon atoms. Examples of the aralkyl groups include benzyl, phenethyl, cinnamyl, and naphtylmethyl.

The alkyl group can be a straight, branched or cyclic alkyl group, can contain an unsaturated bonding, and can have 1 to 16 carbon atoms. Examples of the alkyl groups include methyl, ethyl, propyl, butyl, pentyl, hexyl, heptyl, octyl, cyclopropyl, cyclopentyl, cyclohexyl, cycloheptyl, cyclohexylmethyl, vinyl, propenyl, butenyl, and 1,3-butadienyl.

The heterocyclic group can contain a sulfur atom, an oxygen atom or a nitrogen atom as a ring member and can have 4 to 16 carbon atoms. Examples of the heterocyclic groups include thienyl, furyl, and pyridyl.

In the formula (1), $R^1$, $R^2$, $R^3$ and $R^4$ can be the same or different from each other. Two of $R^1$, $R^2$, $R^3$ and $R^4$ can be combined to form a heterocyclic group containing the phosphor atom as a ring member.

$R^1$, $R^2$, $R^3$ and $R^4$ can be any isomeric group and can have one or more substituents. Examples of the substituents include an alkoxy group preferably having 1 to 12 carbon atoms, a thioalkoxy group preferably having 1 to 12 carbon atoms, an aralkyloxy group preferably having 7 to 13 carbon atoms, an aryloxy group preferably having 6 to 16 carbon atoms, a thioaryloxy group preferably having 6 to 16 carbon atoms, an acyl group preferably having 1 to 12 carbon atoms, an alkoxycarbonyl group preferably having 2 to 16 carbon atoms, a carboxyl group, an amino group, an alkyl-substituted amino group preferably having 2 to 16 carbon atoms, a nitro group, a cyano group, a hydroxyl group, and a halogen atom (e.g., fluorine, chlorine, or bromine).

In the case that one of $R^1$, $R^2$, $R^3$ and $R^4$ is an aromatic ring-containing group such as aryl group, an aralkyl group, or a heterocyclic group, the aromatic group can have one or more of the above-mentioned substituents or can have one or more alkyl groups (preferably having 1 to 12 carbon atoms) which can have a ring (which can be a heterocyclic ring) or an unsaturated bonding. In the case that one of $R^1$, $R^2$, $R^3$ and $R^4$ is a heterocyclic group, the heterocyclic group can have, as a substituent, an aryl group preferably having 6 to 16 carbon atoms.

Examples of the organic phosphonium bromides are described below.

(1) Phosphonium bromide in which all of $R^1$, $R^2$, $R^3$ and $R^4$ are alkyl groups tetraethylphosphonium bromide, tetrabutylphosphonium bromide, and hexadecyltributylphosphonium bromide.

(2) Phosphonium bromide in which some of $R^1$, $R^2$, $R^3$ and $R^4$ are aryl groups and others are alkyl groups methyltriphenylphosphonium bromide, ethyltriphenylphosphonium bromide, propyltriphenylphosphonium bromide, butyltriphenylphosphonium bromide, hexyltriphenylphosphonium bromide, heptyltriphenylphosphonium bromide, tetradecyltriphenylphosphonium bromide, cyclopropyltriphenylphosphonium bromide, allyltriphenylphosphonium bromide, 1,3-butadienyltriphenylphosphonium bromide, and dimethyldiphenylphosphonium bromide.

(3) Phosphonium bromide in which some of $R^1$, $R^2$, $R^3$ and $R^4$ are aryl groups and others are alkyl groups having substituent group(s)

1) The substituent of alkyl is a heterocyclic group
(1,3-dioxolan-2-yl)methyltriphenylphosphonium bromide, 2-(1,3-dioxolan-2-yl)ethyltriphenylphosphonium bromide, and 2-(1,3-dioxan-2-yl)ethyltriphenylphosphonium bromide.

2) The substituent of alkyl is a halogen atom
bromomethyltriphenylphosphonium bromide.

3) The substituent of alkyl is a carboxyl group
4-carboxybutyltriphenylphosphonium bromide and 2-carboxyallyltriphenylphosphonium bromide.

4) The substituent of alkyl is an alkoxycarbonyl group
4-ethoxycarbonylbutyltriphenylphosphonium bromide.

5) The substituent of alkyl is an alkyl-substituted amino group
2-dimethylaminomethyltriphenylphosphonium bromide.

6) The substituent of alkyl is an acyl group
phenacyltriphenylphosphonium bromide.

(4) Phosphonium bromide in which some of $R^1$, $R^2$, $R^3$ and $R^4$ are aryl groups and others are aralkyl groups benzyltriphenylphosphonium bromide, 4-ethoxybenzyltriphenylphosphonium bromide, and cinnamyltriphenylphosphonium bromide.

(5) Phosphonium bromide in which all of $R^1$, $R^2$, $R^3$ and $R^4$ are aryl groups tetraphenylphosphonium bromide, p-biphenyltriphenylphosphonium bromide, 1-naphthyltriphenylphosphonium bromide, and 2-naphthyltriphenylphosphonium bromide.

(6) Phosphonium bromide in which all of $R^1$, $R^2$, $R^3$ and $R^4$ are aryl groups having substituent(s)

1) The substituent of aryl is an alkyl group
o-methylphenyltriphenylphosphonium bromide, m-methylphenyltriphenylphosphonium bromide, p-methylphenyltriphenylphosphonium bromide, p-isopropylphenyltriphenylphosphonium bromide, p-t-butylphenyltriphenylphosphonium bromide, m-trifluoromethylphenyltriphenylphosphonium bromide, and 2,4,6-trimethylphenyltriphenylphosphonium bromide.

2) The substituent of aryl is a halogen atom
p-chlorophenyltriphenylphosphonium bromide.

3) The substituent of aryl is an alkoxy group
m-methoxyphenyltriphenylphosphonium bromide, p-methoxyphenyltriphenylphosphonium bromide, an p-ethoxyphenyltriphenylphosphonium bromide.

4) The substituent of aryl is an amino group
p-aminophenyltriphenylphosphonium bromide.

5) The substituent of aryl is a cyano group
m-cyanophenyltriphenylphosphonium bromide and p-cyanophenyltriphenylphosphonium bromide.

6) The substituent of aryl is a nitro group
p-nitrophenyl-tri-p-tolylphosphonium bromide.

The chloride ion preferably is derived from an alkali metal chloride such as lithium chloride, sodium chloride, potassium chloride, rubidium chloride, or cesium chloride, an alkaline earth metal chloride such as beryllium chloride, magnesium chloride, calcium chloride, or strontium chloride. Otherwise, the chloride ion can be derived hydrogen chloride in an aqueous solution. Preferred are alkali metal chlorides, and most preferred is sodium chloride. The chloride ion source can be a single compound or a combination of two or more compounds.

The chloride ion-containing compound can be employed preferably in an amount of 1 to 500 moles, more preferably in an amount of 5 to 250 moles, most preferably 10 to 200 moles, per one mole of the phosphonium bromide. The chloride ion-containing compound is employed in the form of an aqueous solution in which 1 g of the chloride ion-containing compound is dissolved preferably in 1 to 20 g of water. The amount of the chloride ion-containing compound in the aqueous solution is preferably adjusted to be less than a saturation concentration at the reaction temperature. For instance, 1 g of sodium chloride is preferably dissolved in 2.55 to 20 g of water, more preferably dissolved in 2.79 to 19 g of water.

The aqueous solution containing a chloride ion can be prepared in advance of starting the reaction. Otherwise, a chloride ion-containing compound can be added to a mixture of water and an organic solvent in which the phosphonium bromide can be contained in advance. In the case that an aqueous solution containing a chloride ion is prepared in advance, the chloride ion-containing compound can be added to the whole amount of water. Otherwise, the chloride ion-containing compound can be added to a portion of water in an amount not to reach the saturation concentration, and thus prepared aqueous solution can be mixed with an aqueous mixture solution containing an organic solvent in which a phosphonium bromide and a chloride ion are contained.

The organic solvent employed in the invention should not give a homogenous solution with water, in the presence of phosphonium salts (starting phosphonium bromide and resulting phosphonium chloride) and a chloride ion in amounts for performing the reaction. The organic solvent can be employed singly or in combination.

The organic solvent preferably is an alcohol (aliphatic alcohol or aromatic alcohol) having 2 or more carbon atoms (preferably 2 to 12 carbon atoms), a halogenated aliphatic hydrocarbon, a nitrile compound, an amide compound, a urea compound having 5 or more carbon atoms. Preferred are an alcohol having 2 or more carbon atoms and a halogenated aliphatic hydrocarbon. Most preferred is an alcohol having 2 or more carbon atoms.

The alcohol having 2 or more carbon atoms preferably is an aliphatic alcohol (i.e., alkyl alcohol) having 2 to 12 carbon atoms or an aromatic-aliphatic alcohol (i.e., aralkyl alcohol) having 7 to 12 carbon atoms. Examples of the preferred alcohols include ethanol, 1-propanol, 2-propanol, 1-butanol, 2-butanol, 2-methyl-1-propanol, 1,1-dimethylethanol, 1-pentanol, 2-pentanol, 3-pentanol, 3-methyl-1-butanol, 2-methyl-1-butanol, 1,1-dimethyl-1-propanol, 1-hexanol, 2-hexanol, 3-hexanol, 2-methyl-1-pentanol, 4-methyl-2-pentanol, 1-heptanol, 2-heptanol, 3-heptanol, 4-heptanol, 1-octanol, 2-octanol, 2-ethyl-1-hexanol, 1-nonanol, 2-nonanol, 1-decanol, 1-undecanol, 1-dodecanol, 1,6-hexanediol, cyclopentanol, cyclohexanol, benzyl alcohol, 1-phenylethanol, and 3-phenylethanol.

Most preferred are aliphatic alcohols having 3 to 6 carbon atoms, in which a phosphonium salt is easily soluble, an aqueous solution hardly is miscible, and the reaction to give a phosphonium chloride smoothly proceeds.

The halogenated aliphatic hydrocarbon preferably has 1 to 10 carbon atoms. Examples of the preferred halogenated aliphatic hydrocarbons include methylene chloride, chloroform, 1,2-dichloroethane, 1,1,1-trichloroethane, 1,1,2-trichloroethane, 1,2-dichloropropane, 1,3-dichloropropane, 1,2,3-trichloropropane, 1,4-dichlorobutane, and 1,6-dichlorohexane.

The nitrile compound preferably is an aliphatic nitrile compound having 1 to 8 carbon atoms and an aromatic nitrile having 6 to 12 carbon atoms. Examples of the preferred nitrile compounds include acetonitrile, propionitrile, butyronitrile, adiponitrile, and benzonitrile.

The amide compound preferably is an aliphatic amide compound having 3 to 6 carbon atoms. Examples of the amide compounds include dimethylformamide and dimethylacetamide.

The urea compound preferably is an aliphatic urea compounds having 5 to 9 carbon atoms. Examples of the urea compounds include tetramethylurea and 1,3-dimethylimidazolidin-2-one.

The organic solvent can be employed in combination with an organic solvent in which the phosphonium bromide is not soluble. Examples of the latter organic solvents (i.e., secondary organic solvent) include aromatic hydrocarbons such as benzene, toluene, xylene, ethylbenzene, isopropylbenzene, and methylnaphthalene, halogenated aromatic hydrocarbons such as chlorobenzene and o-dichlorobenzene, ketones such as acetone and methyl ethyl ketone, esters such as ethyl acetate and butyl acetate, and ethers such as diethyl ether, diisopropyl ether, dibutyl ether, and diphenyl ether.

The secondary organic solvent can be employed in an amount of 0.2 to 100 g, preferably 0.5 to 50 g, more preferably 1 to 25 g, per 1 g of the phosphonium bromide. The solvent can be repeatedly employed after recovery from the reaction mixture, for example, by distillation.

In the reaction, the phosphonium bromide is brought into contact with an aqueous solution containing a chloride ion. This procedure can be performed by bringing an organic solvent solution containing the phosphonium bromide batchwise or continuously into contact with an aqueous solution containing a chloride ion. The procedure can be done once or more times. The contact can be performed, for instance, 1 to 50 times, preferably 2 to 30 times, more preferably 3 to 20 times. The contact is preferably performed under stirring so that the reaction rate is accelerated. One contact procedure can be performed, for instance, for 0.001 to 6 hours, preferably 0.005 to 3 hours, more preferably 0.01 to 1 hour.

The reaction temperature for the contact between the phosphonium bromide and the chloride ion-containing aqueous solution varies depending on the organic solvent (also the secondary organic solvent) to be employed in combination and/or pressure but preferably is –20 to 150° C., more preferably 0 to 100° C. The reaction temperature is preferably selected to satisfy the condition that the organic solvent is kept under liquid condition and any of the chloride ion-containing compound, phosphonium bromide and phosphonium chloride are not separated to give a solid deposit. The reaction can be performed under reduced pressure, under atmospheric pressure, or under elevated pressure. In view of available reaction vessel and easiness of procedure, an atmospheric pressure or an elevated pressure up to 10 kg/cm$^2$ is preferably employed.

After the contact between the phosphonium bromide and the halide ion-containing aqueous solution, the produced phosphonium chloride is easily recovered from an organic layer (i.e., a layer of an organic solution containing the produced phosphonium chloride) which is separated from the aqueous layer. For instance, the organic layer is separated and subjected to distillation to distill the organic solvent off, to give the desired phosphonium chloride as a residue. Otherwise, the separated organic solution can be chilled to deposit the desired phosphonium chloride as a solid product. Also employable is that the organic solvent in which the phosphonium chloride is soluble is removed from the separated organic solution by distillation, and to the remaining residue is added an organic solvent in which the phosphonium chloride is sparingly soluble, to separate out the phosphonium chloride as a solid deposit. Also employable is that an organic solvent in which the phosphonium chloride is sparingly soluble is directly added to the separated organic solution, to separate out the phosphonium chloride as a solid deposit. Further employable is that an organic solvent in which the phosphonium chloride is sparingly soluble is added to the separated organic solution, and the organic solvent in which the phosphonium chloride is sparingly soluble and the organic solvent in which the phosphonium chloride is easily soluble both are distilled off by azeotropic distillation, to separate out the phosphonium chloride as a solid deposit.

Examples of the solvents in which the phosphonium chloride is sparingly soluble include the solvents which are mentioned as the secondary solvent as an optionally employable solvent for the reaction. The solvent can be employed singly or in combination, and employed preferably in a volume amount of 0.1 to 20 mL, more preferably 0.1 to 10 mL, per 1 g of the phosphonium chloride. If the produced phosphonium chloride is sparingly soluble in water, water can be employed in a similar amount in place of the organic solvent.

In the case that the solvent in which the phosphonium chloride is easily soluble is still present in the residual solution after distilling the solvent off from the separated organic solution, water can be added to the residual solution for easily recovering the phosphonium chloride from the residual solution. In this case, water can be employed generally in an amount of 0.1 to 6 moles, preferably 0.5 to 5 moles, more preferably 1 to 4 moles, per one mole of the starting phosphonium bromide. Water can contain hydrogen chloride in an amount of one mole or less, preferably, 0.0001 to 1 mole, more preferably 0.0005 to 1 mole, per one mole of the starting phosphonium bromide.

In the case that the chloride ion-containing compound is present in the separated organic solution, a solvent in which the phosphonium chloride is easily soluble but the chloride ion-containing compound is sparingly soluble can be added to the organic solution, and then the deposited chloride ion-containing compound is removed, for instance, by decantation, filtration, or centrifugal procedure. For example, the organic solvent is distilled off from the organic solution, a halogenated aliphatic hydrocarbon such as methylene chloride, chloroform, or 1,2-dichloroethane is added to the residue to dissolve the residue in the hydrocarbon, and the separated insoluble solid is removed. Otherwise, the separated organic solution is optionally subjected to distillation for distilling the organic solvent off, an aromatic hydrocarbon such as benzene, toluene, xylene, ethylbenzene, or chlorobenzene is added to the organic solution or its residue at an appropriate temperature so as to dissolve the phosphonium chloride, and the insolubles are separated out so that the chloride ion-containing compound is removed.

The phosphonium chloride produced by the aforementioned reaction and recovered by one of the above-mentioned procedures can be further purified, if necessary, by recrystallization or precipitation. The solvents employed in the reaction and the phosphonium chloride recovery procedure can be recovered and repeatedly employed, if necessary, after removal of water.

The present invention is further illustrated by the following examples. In the following examples, the procedures were performed at an ambient temperature and at an atmospheric pressure, unless otherwise mentioned. The amounts of bromide ion and chloride ion were determined by potentiometric titration using an aqueous silver nitrate solution (0.01 mol/1 liter). The phosphonium bromide was prepared by a known process by the reaction between a tertiary phosphine and a bromide compound (Chem. Ber., 99, pp. 2782 (1966)).

EXAMPLE 1

In a 2 liter-volume glass separating funnel, tetraphenylphosphonium bromide (357.74 mmol.), 1-butanol (750 mL), ion-exchanged water (40 mL), and an aqueous 25 wt. % sodium chloride solution (375 mL) were placed, and the content was stirred for 45 minutes at room temperature under heterogenous conditions. The resulting reaction mixture had two layers. The reaction mixture was further stirred for 7 minutes, and allowed to stand. The lower layer (aqueous layer) was removed, and to the remaining upper layer (organic solution layer) was added an aqueous 25 wt. % sodium chloride solution (375 mL). The mixture was stirred for 7 minutes, and the lower layer (aqueous layer) was removed. To the remaining organic solution layer was again added an aqueous 25 wt. % sodium chloride solution (375 mL), and the lower layer was removed after stirring for 7 minutes. The same separation procedure was repeated 6 times.

The finally separated organic solution was subjected to distillation to distill 566 g of 1-butanol containing water off. The residue containing deposited solid was heated on an oil bath (120°C.) under stirring after addition of xylene (100 mL). The solution was filtered on a glass filter (heated to 90°C.) to obtain a filtrate. The solid collected on the filter was washed with a heated mixture (90° C.) of 1-butanol (15 mL) and xylene (15 mL). The filtrate and washings were combined and concentrated under reduced pressure to distill the solvent (99.42 g) off. The residue was again concentrated to distill the solvent (91.87 g) off, after addition of xylene (100 mL).

The residual slurry was stirred after addition of xylene (250 mL) and water (13 mL). The precipitated solid was collected on a filter by suction, and washed twice with xylene (50 mL). The washed solid was dried by applying heated air (65° C.) and further dried under reduced pressure at 65 to 200° C., to obtain the desired tetraphenylphosphonium chloride (yield: 95.9%). Analysis of the halide ion content of the obtained product indicated that 99 molar % or more of the halide ion was chloride ion and no bromide ion was detected (less than 1 molar %).

EXAMPLE 2

In a 100 mL-volume glass separating funnel, tetraphenylphosphonium bromide (23.85 mmol.) and 1-butanol (50 mL) were placed, and the content was heated to 60° C. to give a homogeneous solution. The resulting homogeneous solution was allowed to stand until the temperature reached room temperature. To the solution were added ion-exchanged water (3 mL) and an aqueous 25 wt. % sodium chloride solution (25 mL), and the mixture was stirred for 4 minutes. The mixture was then allowed to stand for separating an upper layer (organic solution layer) from a lower layer (aqueous layer). The lower aqueous layer was removed. To the remaining organic solution layer was added an aqueous 25 wt. % sodium chloride solution (25 mL). The mixture was then stirred for 4 minutes and allowed to stand for separation. The lower layer (aqueous layer) was then removed. The same separation procedure was repeated 6 times.

The finally separated organic solution was subjected to distillation to distill 1-butanol containing water off. The residue (viscous slurry) was dissolved in methylene chloride (30 mL), and insolubles were filtered off on a glass filter. The insolubles on the filter were washed with methylene chloride (5 mL). The washings and the filtrate were combined and concentrated under reduced pressure to distill methylene chloride off.

The residue was filtered by suction to collect a solid on the filter after addition of toluene (30 mL), diethyl ether (10 mL), and water (1 mL). The collected solid was heated to 65–180° C. to dryness under reduced pressure, yielding the desired tetraphenylphosphonium chloride (yield: 94.3%). Analysis of the halide ion content of the obtained product indicated that 99 molar % or more of the halide ion was chloride ion and no bromide ion was detected (less than 1 molar %).

EXAMPLE 3

In a 2 liter-volume glass separating funnel, tetraphenylphosphonium bromide (536.61 mmol.) and 1-butanol (1,125 mL) were placed, and the content was stirred for 30 minutes to give a homogeneous solution. To the resulting homogeneous solution were added ion-exchanged water (60 mL) and an aqueous 25 wt. % sodium chloride solution (562.5 mL), and the mixture was stirred for 10 minutes. The mixture was then allowed to stand for separating an upper layer (organic solution layer) from a lower layer (aqueous layer). The lower aqueous layer was removed. To the remaining organic solution layer was added an aqueous 25 wt. % sodium chloride solution (562.5 mL). The mixture was then stirred for 7 minutes and allowed to stand for separation. The lower layer (aqueous layer) was then removed. The same separation procedure was repeated 6 times.

The finally separated organic solution was subjected to distillation to distill 1-butanol (849 g) containing water off. The residue containing deposited solid was heated on an oil bath (120° C.) under stirring after xylene (150 mL) was dropwise added for 20 minutes. The mixture was stirred for 20 minutes at the same temperature, and filtered on a glass filter (heated to 90° C.) to obtain a filtrate. The solid collected on the filter was washed with a heated mixture (90° C.) of 1-butanol (18 mL) and xylene (27 mL). The filtrate and washings were combined and concentrated at 170–177° C. (bath temperature) under reduced pressure to distill the solvent (325 mL) off. In the course of the distillation, xylene (150 mL) was dropwise added to the residue for 40 minutes, after 175 mL of the solvent was distilled off. The bath was cooled to 130° C., and to the residue was added xylene (300 mL) for 30 minutes under stirring. The bath was further cooled to 95° C., and to the stirred solution was dropwise added an aqueous hydrochloric acid (which was prepared from 1 mL of 35 wt. % hydrochloric acid and 9 mL of ion-exchanged water) for 15 minutes.

The bath was cooled to room temperature, while the mixture was stirred. The deposited solid was collected on a filter by suction and washed with xylene (75 mL) two times. Thus obtained solid was dried by applying hot air (65–100° C.) and then heated to 65–230° C. to dryness under reduced pressure, yielding the desired tetraphenylphosphonium chloride (yield: 97.6%). Analysis of the halide ion content of the obtained product indicated that 99 molar % or more of the halide ion was chloride ion and no bromide ion was detected (less than 1 molar %).

EXAMPLE 4

In a 2 liter-volume glass separating funnel, tetraphenylphosphonium bromide (536.61 mmol.), 1-butanol (204 mL), the 1-butanol containing water (849 g, water content 103 g) which was recovered in Example 3, an aqueous 25 wt. % sodium chloride solution (514 mL), and sodium chloride (14.32 g) were placed, and the content was stirred for 1 hour to dissolve the solid content in the mixture solution. The mixture was further stirred for 10 minutes and allowed to stand for separating an upper layer (organic solution layer) from a lower layer (aqueous layer). The lower aqueous layer was removed. To the remaining organic solution layer was added an aqueous 25 wt. % sodium chloride solution (562.5 mL). The mixture was then stirred for 7 minutes and allowed to stand for separation. The lower layer (aqueous layer) was then removed. The same separation procedure was repeated 6 times.

The finally separated organic solution was subjected to distillation to distill 1-butanol (958.61 g) containing water off. The solid residue (216.13 g) was dissolved in methylene chloride (400 mL), and insolubles were filtered off on a glass filter. The insolubles on the filter were washed with methylene chloride (40 mL). The washings and the filtrate were combined and concentrated at 50–80° C., first at an atmospheric pressure and then under reduced pressure (300–25 mmHg), to distill methylene chloride off.

The solid residue was pulverized and heated to 60–200° C. to dryness under reduced pressure, yielding the desired tetraphenylphosphonium chloride (yield: 98.2%). Analysis of the halide ion content of the obtained product indicated that 99 molar % or more of the halide ion was chloride ion and no bromide ion was detected (less than 1 molar %).

EXAMPLE 5

In a 100 mL-volume glass separating funnel, tetraphenylphosphonium bromide (23.85 mmol.) and methylene chloride (50 mL) were placed, and the content was vigorously shaken after addition of an aqueous 23.3 wt. % sodium chloride solution (20 mL). The mixture was then allowed to stand to separate a lower layer (organic solution layer) from an upper layer (aqueous layer). The upper aqueous layer was removed. To the remaining organic solution layer was added an aqueous 23.3 wt. % sodium chloride solution (20 mL). The mixture was then shaken vigorously and allowed to stand for separation. The upper layer (aqueous layer) was then removed. The same separation procedure was repeated 8 times.

The finally separated organic solution was dried over anhydrous magnesium sulfate. The magnesium sulfate was removed by filtration and the filtrate was subjected to distillation to distill methylene chloride off.

The residual solid was heated to 56–200° C. to dryness under reduced pressure, yielding the desired tetraphenylphosphonium chloride (yield: 96.7%). Analysis of the halide ion content of the obtained product indicated that 82 molar % of the halide ion was chloride ion and 18 molar % was bromide ion.

EXAMPLE 6

In a 2 liter-volume glass separating funnel, tetraphenylphosphonium bromide (357.74 mmol.) and 1-butanol (1,125 mL) were placed, and the content was stirred for 30 minutes to give a homogeneous solution. To the resulting homogeneous solution were added ion-exchanged water (60 mL) and an aqueous 25 wt. % sodium chloride solution (562.5 mL), and the mixture was stirred for 10 minutes. The mixture was then allowed to stand for separating an upper layer (organic solution layer) from a lower layer (aqueous layer). The lower aqueous layer was removed. To the remaining organic solution layer was added an aqueous 25 wt. % sodium chloride solution (562.5 mL). The mixture was then stirred for 7 minutes and allowed to stand for separation. The lower layer (aqueous layer) was then removed. The same separation procedure was repeated 6 times.

The finally separated organic solution was subjected to distillation to distill 1-butanol (846.74 g) containing water off. To the residue containing deposited solid was added xylene (150 mL), and the mixture was stirred at 75° C. for 20 minutes. The mixture was then filtered on a glass filter (heated to 75° C.) to obtain a filtrate. The solid collected on the filter was washed with a heated mixture (75° C.) of 1-butanol (9 mL) and xylene (13.5 mL). The filtrate and washings were combined and concentrated at 170–177° C. (bath temperature) under reduced pressure to distill the solvent (300 mL) off. In the course of the distillation, xylene (150 mL) was dropwise added to the residue for 40 minutes, after 150 mL of the solvent was distilled off. The bath was cooled to 105° C, and to the residue was dropwise added a mixture of 36 wt. % hydrochloric acid (1.5 mL) and ion-exchanged water (28.5 mL) for 15 minutes.

The bath was cooled to 90° C. for 15 minutes. To the mixture was then added xylene (250 mL) for 45 minutes, while the mixture was stirred. The mixture was cooled to reach room temperature, while the mixture was stirred. The deposited solid was collected on a filter by suction and washed with xylene (75 mL) two times. Thus obtained solid was dried by applying hot air (65–120° C.) and then heated to 65–200° C. to dryness under reduced pressure, yielding the desired tetraphenylphosphonium chloride (yield: 97.3%). Analysis of the halide ion content of the obtained product indicated that 99 molar % or more of the halide ion was chloride ion and no bromide ion was detected (less than 1 molar %).

EXAMPLE 7

In a 100 mL-volume glass separating funnel, p-t-butylphenyltriphenylphosphonium bromide (21.03 mmol.) and isopropanol (50 mL) were placed, and the content was vigorously shaken after addition of an aqueous 25.9 wt. % sodium chloride solution (20 mL) and ion-exchanged water (11 mL). The mixture was then allowed to stand for separating an upper layer (organic solution layer) from a lower layer (aqueous layer). The lower aqueous layer was removed. To the remaining organic solution layer were added an aqueous 25.9 wt. % sodium chloride solution (20 mL) and ion-exchanged water (3 mL). The mixture was vigorously shaken and allowed to stand for separation. The lower layer (aqueous layer) was then removed. The same separation procedure was repeated 7 times, under the condition that 2 mL of ion-exchanged water was added in the second, fourth, fifth, and seventh separation procedure.

The finally separated organic solution was concentrated under reduced pressure, and the solid residue was recrystallized from ion-exchanged water (18 mL). The precipitated crystalline product was collected on a filter by suction. The crystalline product was washed with ion-exchanged water (10 mL) two times, and heated to 65–170° C. to dryness under reduced pressure, yielding the desired p-t-butylphenyltriphenylphosphonium chloride (yield: 95%). Analysis of the halide ion content of the obtained product indicated that 99 molar % or more of the halide ion was chloride ion and no bromide ion was detected (less than 1 molar %).

EXAMPLE 8

In a 2 liter-volume glass separating funnel, p-t-butylphenyltriphenylphosphonium bromide (421.05 mmol.) and isopropanol (1,000 mL) were placed, and the content was stirred for 30 minutes to give a homogeneous solution. To the resulting homogeneous solution were added ion-exchanged water (180 mL) and an aqueous 24.5 wt. % sodium chloride solution (450 mL), and the mixture was stirred for 7 minutes. The mixture was then allowed to stand for separating an upper layer (organic solution layer) from a lower layer (aqueous layer). The lower aqueous layer was removed. To the remaining organic solution layer was added an aqueous 24.5 wt. % sodium chloride solution (450 mL). The mixture was then stirred for 7 minutes and allowed to stand for separation. The lower layer (aqueous layer) was then removed. To the remaining organic solution was added an aqueous 25 wt. % sodium chloride solution (562.5 mL). The mixture was then stirred for 7 minutes and allowed to stand for separation. The lower layer (aqueous layer) was then removed. The same separation procedure was repeated 6 times.

The finally separated organic solution was subjected to distillation to distill isopropanol (511.43 g) containing water off. To the residue was added at 85–90° C. under stirring ion-exchanged water (360 mL) for 30 minutes. The mixture was subjected to distillation to distill isopropanol (154.1 g) containing water off. To the residual solution was then added ion-exchanged water (100 mL), and the aqueous mixture was subjected to distillation to distill 100 mL of water-containing isopropanol off. This procedure was repeated twice.

To the residual solution were dropwise added at 90–104° C. under stirring ion-exchanged water (100 mL) and 36 wt. % hydrochloric acid (1.5 mL). The aqueous mixture was cooled to room temperature and then chilled using a ice-water mixture.

The deposited solid was collected on a filter by suction and washed with ion-exchanged water (70 mL) three times. The washed solid was dried by applying air heated to 65–120° C., and then heated to 100–180° C. to dryness under reduced pressure, yielding the desired p-t-butylphenyltriphenylphosphonium chloride (yield: 95.8%). Analysis of the halide ion content of the obtained product indicated that 99 molar % or more of the halide ion was chloride ion and no bromide ion was detected (less than 1 molar %).

What is claimed is:

1. A process for preparing an organic phosphonium chloride which comprises bringing an organic phosphonium bromide into contact with a chloride ion in a heterogeneous mixture solution comprising water and an organic solvent.

2. The process of claim 1, wherein the chloride ion is that of an alkali metal chloride.

3. The process of claim 1, wherein the chloride ion is that of sodium chloride.

4. The process of claim 1, wherein the organic solvent is an alcohol having 2 to 12 carbon atoms, an aliphatic hydrocarbon halide having 1 to 10 carbon atoms, an aliphatic or aromatic nitrile compound having 1 to 8 carbon atoms, an aliphatic amide compound having 3 to 6 carbon atoms, or an aliphatic urea compound having 5 to 9 carbon atoms.

5. The process of claim 1, wherein the organic phosphonium chloride is a tetraarylphosphonium chloride and the organic phosphonium bromide is a tetraarylphosphonium bromide.

6. The process of claim 1, wherein the organic phosphonium chloride is tetraphenylphosphonium chloride and the organic phosphonium bromide is tetraphenylphosphonium bromide.

7. The process of claim 1, wherein the organic phosphonium chloride is p-t-butylphenyltriphenylphosphonium chloride and the organic phosphonium bromide is p-t-butylphenyltriphenylphosphonium bromide.

8. The process of claim 1, wherein the organic solvent is an aliphatic alcohol having 3 to 6 carbon atoms.

9. A process for preparing an organic phosphonium chloride which comprises the steps of:

bringing an organic phosphonium bromide into contact with a chloride ion in a heterogeneous mixture solution comprising water and an organic solvent to prepare an organic phosphonium chloride;

separating the heterogenous solution into an aqueous part and an organic solution part; and recovering the resulting organic phosphonium chloride from the organic solution part.

* * * * *